US008652322B2

(12) United States Patent
Jurio et al.

(10) Patent No.: US 8,652,322 B2
(45) Date of Patent: Feb. 18, 2014

(54) MULTI-COMPONENT PART TRANSDUCER ASSEMBLY AND A METHOD FOR DETERMINING THE PRESSURE OF A FLUID USING THE TRANSDUCER

(75) Inventors: Javier Jurio, Uppsala (SE); Roger Lundqvist, Alunda (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 539 days.

(21) Appl. No.: 12/744,387

(22) PCT Filed: Nov. 26, 2008

(86) PCT No.: PCT/SE2008/000663
§ 371 (c)(1),
(2), (4) Date: May 24, 2010

(87) PCT Pub. No.: WO2009/070085
PCT Pub. Date: Jun. 4, 2009

(65) Prior Publication Data
US 2010/0252491 A1  Oct. 7, 2010

(30) Foreign Application Priority Data

Nov. 27, 2007  (GB) .................................. 0723205.1

(51) Int. Cl.
*B01D 35/14*  (2006.01)
*G01L 19/14*  (2006.01)

(52) U.S. Cl.
USPC ....... 210/90; 210/198.2; 210/263; 210/321.6; 210/741; 73/715; 73/756; 73/866.5

(58) Field of Classification Search
USPC .................. 73/715, 716, 756, 861.47, 866.5; 361/283.4; 340/611, 614; 324/439; 210/85, 90, 96.1, 96.2, 198.2, 263, 210/321.6, 741

See application file for complete search history.

(56) References Cited

U.S. PATENT DOCUMENTS

| | | | |
|---|---|---|---|
| 2,916,715 A * | 12/1959 | Nunn | 338/41 |
| 3,723,305 A * | 3/1973 | Radford | 210/646 |
| 4,539,849 A | 9/1985 | Pike | |
| 4,545,389 A | 10/1985 | Schaberg et al. | |
| 5,868,678 A | 2/1999 | Brunner et al. | |
| 6,280,406 B1 * | 8/2001 | Dolecek et al. | 604/4.01 |
| 7,313,968 B2 | 1/2008 | Kaneko et al. | |
| 2002/0104786 A1 * | 8/2002 | Chevallet | 210/86 |
| 2003/0200812 A1 | 10/2003 | Kuhn et al. | |
| 2005/0284815 A1 * | 12/2005 | Sparks et al. | 210/645 |
| 2006/0258960 A1 * | 11/2006 | Turnbull et al. | 600/587 |
| 2007/0074592 A1 * | 4/2007 | Santos | 73/866.5 |
| 2009/0010627 A1 * | 1/2009 | Lindsay et al. | 392/466 |

FOREIGN PATENT DOCUMENTS

| | | |
|---|---|---|
| EP | 1 400 254 | 3/2004 |
| JP | 4-346044 | 1/1992 |
| WO | WO 98/47424 | 10/1998 |
| WO | WO 99/13926 | 3/1999 |
| WO | WO 2004/089518 | 10/2004 |
| WO | WO 2005/003710 | 1/2005 |

* cited by examiner

*Primary Examiner* — Joseph Drodge

(57) ABSTRACT

The invention relates to a multi-component part transducer assembly for determining the pressure of a fluid of interest. One part of the assembly comprises a reusable transducer, another part a disposable component comprising a flexible membrane which is in pressure connection with the fluid of interest, and another part comprises a locking component for securing the reusable and disposable parts together.

22 Claims, 3 Drawing Sheets

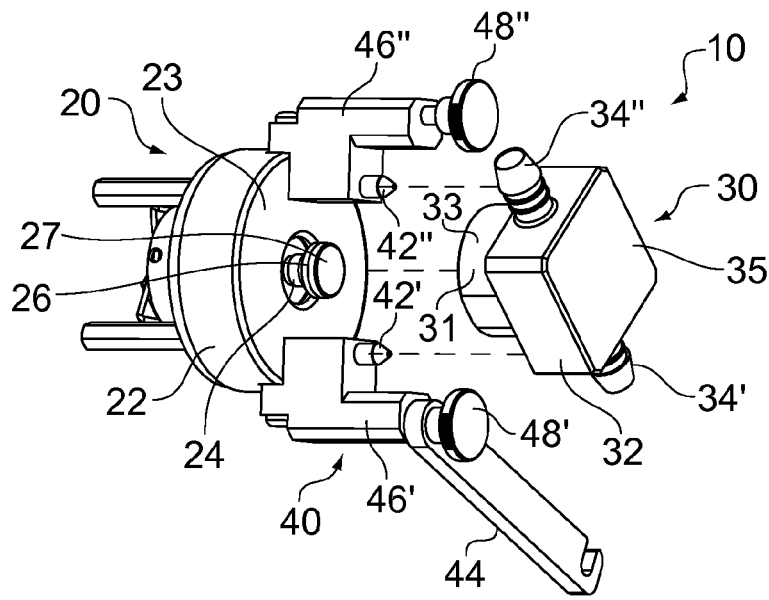
FIG. 1a
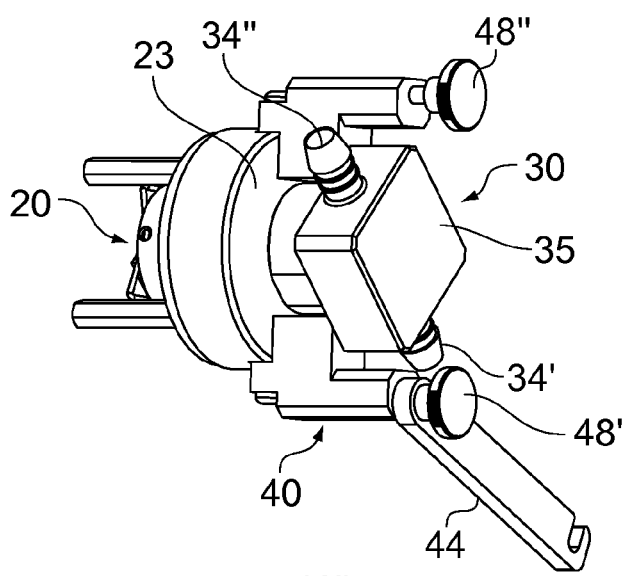
FIG. 1b
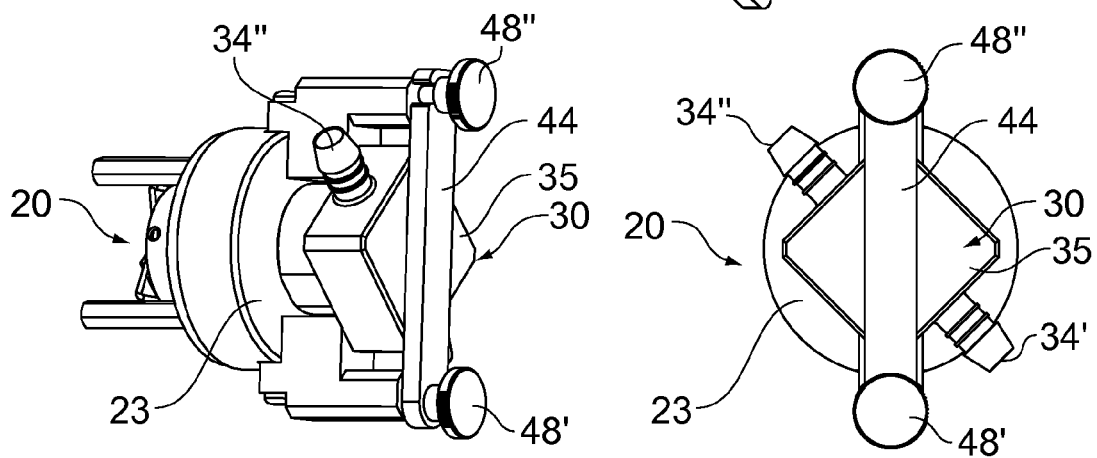
FIG. 1c
FIG. 1d

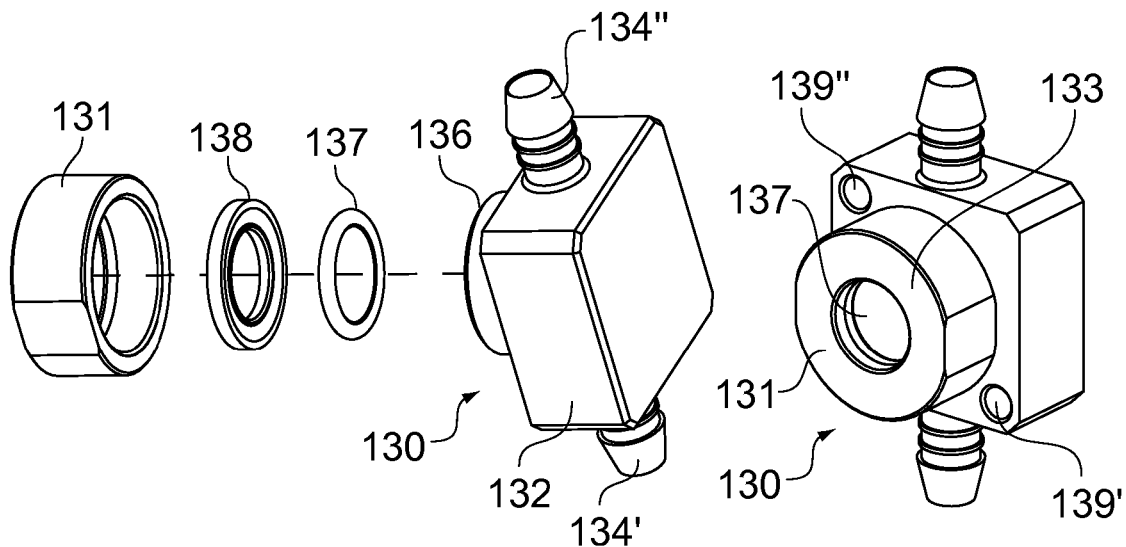
FIG. 2a   FIG. 2b
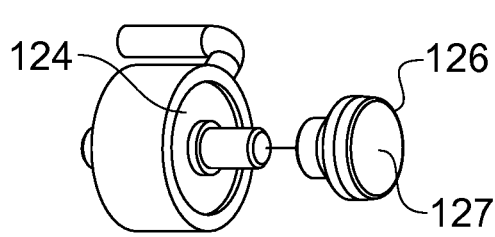   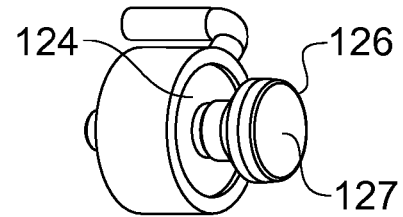
FIG. 2c   FIG. 2d
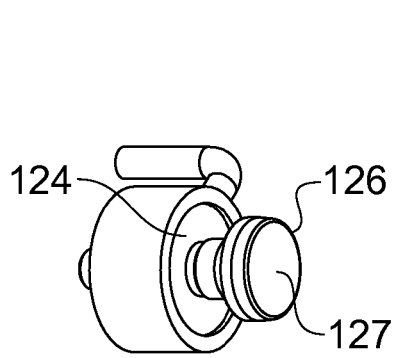   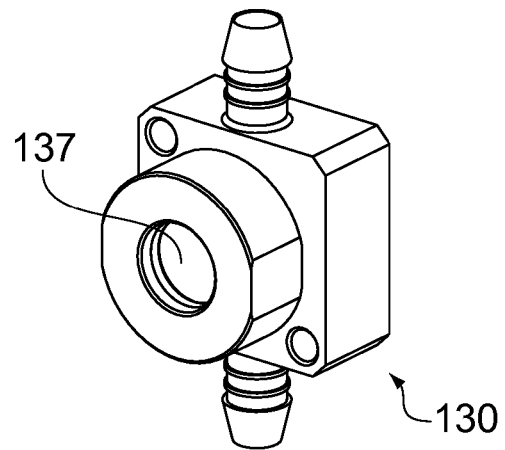
FIG. 2e   FIG. 2f

MULTI-COMPONENT PART TRANSDUCER ASSEMBLY AND A METHOD FOR DETERMINING THE PRESSURE OF A FLUID USING THE TRANSDUCER

CROSS-REFERENCE TO RELATED APPLICATIONS

This application is a filing under 35 U.S.C. §371 and claims priority to international patent application number PCT/SE2008/000663 filed Nov. 26, 2008, published on Jun. 4, 2009, as WO 2009/070085, which claims priority to patent application number 0723205.1 filed in Sweden on Nov. 27, 2007.

FIELD OF THE INVENTION

The present invention relates to a multi-component part transducer assembly for determining the pressure of a fluid of interest. The multi-component part transducer assembly of the invention is of particular use in the development and manufacture or pharmaceutical and biotechnological products, where it is suitable for use in a wide range of applications including chromatographic separations, filtration, dialysis and chemical synthesis.

BACKGROUND OF THE INVENTION

Good manufacturing practices (GMP) and governmental regulations are key to any pharmaceutical or biotechnological development or manufacturing process or procedure today. Such processes and procedures, together with the associated equipment, must undergo mandatory validation and qualification procedures to satisfy the regulatory authorities. Thus, for example, the equipment used for the separation and purification of biomedical products, such as preparative chromatography or tangential flow filtration systems, must meet stringent cleanliness requirements involving multiple tests for microbiological contamination. Additional safeguards must also be implemented to avoid chemical cross-contamination between product runs using the same equipment. These procedures are both costly and time consuming.

In order to reduce such cleaning and validation costs and expenses, the pharmaceutical and biotechnology industries are increasingly using pre-sterilised, single-use or disposable equipment in their separation and purification processes. There is therefore a need for inexpensive, disposable sensors which can be pre-sterilised and used in such processes.

Disposable pressure transducers are commonly used in medical environments for measuring body fluid pressures, particularly blood pressures, outside the patient's body. These transducers typically consist of a disposable part, which is inexpensive to manufacture, and a reusable part which comprises the expensive, electronic sensor. The disposable part generally consists of a flexible membrane or diaphragm which in use is placed in pressure contact both with the patient's body fluid, via capilliary tubing or a catheter, and a second diaphragm affixed to the reusable sensor. When the two diaphragms are in pressure contact, the sensor converts the pressure in the body fluid into the corresponding electrical signal and thereby provides a measurement of pressure which can be read as a visual output.

Thus, for example, U.S. Pat. No. 5,868,678 (Medex, Inc.) describes a medical pressure transducer in which a disposable fluid path component such as a dome is selectively attachable to a reusable pressure sensor component with respective fluid pressure communicating diaphragms of the components in a pressure communicating relationship. The two components are designed to be slid together by translation along a generally straight line, rather than by relative rotation, in order to reduce wear on the reusable diaphragm.

While such pressure transducers are suitable for measuring the pressure of body fluids, their accuracy or sensitivity is dependent upon both the area and degree of overlap between the two flexible membranes or diaphragms. If, for example, the membranes are not aligned axially then the pressure transmitted to the sensor may not be measured correctly. Furthermore, the linearity of signal detected may be compromised if the flexibility of one or both membranes varies across their surface and is thus more responsive to pressure in one region of the membrane (e.g. the centre).

Another problem with the pressure transducers used in the prior art is that they have a limited operating range associated with the pressure of the body fluids that they are measuring. While they are suitable for use at relatively low pressures (e.g. $<5 \times 10^4$ Pa; 0.5 bar) they cannot be used for measuring higher pressures (e.g. in excess of $4 \times 10^5$ Pa, 4 bar associated with bioseparations and filtrations). Different pressure transducers are therefore necessary to measure both low and high pressures.

The component parts of the prior art transducers are generally attached to each other by snap-on connectors which can only withstand relatively low forces acting on them to pull them apart. Moreover, the capillary tubing used with these transducers tends to rupture at high pressures and flow rates. Separation, filtration, dialysis and synthesis applications used in bio-separations, for example, must typically be able to accurately measure pressures in excess of $4 \times 10^5$ Pa and to reliably operate at such pressures. Furthermore, the component parts of such transducers must be able to withstand forces of at least 10 N, and preferably at least 50 N, acting to separate them when they are in operable contact.

There is therefore a need within the pharmaceutical and biotechnological industries for a multi-part transducer assembly which overcomes the failings of those known in the prior art.

SUMMARY OF THE INVENTION

In a first aspect of the present invention, there is provided a multi-component part transducer assembly for determining the pressure in a fluid of interest, the assembly comprising a reusable component comprising a transducer;

a disposable component comprising a body having a container or conduit therein which defines a flow path for the fluid and a flexible membrane in pressure contact with the fluid; and a locking component to secure the reusable component to the disposable component in order to effect pressure contact between the transducer and the flexible membrane;

wherein the transducer is a load cell.

The use of a load cell, which has a rigid face rather than an elastomeric diaphragm for pressure contact with the flexible membrane, provides a more accurate measurement than prior art transducers because the rigid face has uniform sensitivity across its surface which improves the linearity of the signal received.

Preferably, the reusable component additionally comprises an adapter attachable to the load cell having one face for contact with the flexible membrane to effect pressure contact between the flexible membrane and the load cell. The use of such adapters, which can be selected based upon the pressure to be determined in the flow path, permits the effective exploitation of the load cell range. Thus, the user can determine both low (e.g. <$5\times10^4$ Pa, 0.5 bar) and high (e.g. >$5\times10^5$ Pa, 5 bar) pressures in the flow path, depending upon the particular application, with the same load cell by simply changing the adapter to correspond to the size of the membrane in the flow path. It will be understood that the load cell determines the pressure in the flow path by means of the relationship: Force=Pressure×Area, thus by measuring the force exerted on the flexible membrane in the flow cell and by knowing the area of the load cell/adapter face in contact with the membrane, the pressure in the flow cell can be determined.

More preferably the one face of the adapter is modified to maximise contact between the face and the flexible membrane. Most preferably, the one face of the adapter is either planar or convex. A slightly convex face assists the removal of air bubbles, if present, which may be adjacent to the interior face of the flexible membrane and which may affect the measurement of pressure.

Preferably, the adapter is reversibly attachable to the load cell. The adapter may be attachable to the load cell by a number of means, including for example by a screw thread or snap fit.

Preferably, the area of the one face of the adapter can be varied to correspond to the area of the flexible membrane.

Preferably, the assembly is for use in a pharmaceutical or biotechnology development or manufacturing facility.

Preferably, the disposable component is securable to the reusable component by the locking component such that a force of at least 10 N (preferably of at least 50 N) is required to separate the disposable component from the reusable component.

Suitably, the locking component is a yoke.

Preferably, the flow path has an internal diameter in excess of 3 mm, more preferably an internal diameter in excess of 6 mm Suitably, the flow path is connected to reinforced tubing. Preferably, the reinforced tubing is capable of withstanding a pressure of at least $4\times10^5$ Pa (4 bars). More preferably, the reinforced tubing is capable of withstanding a pressure of at least $5\times10^5$ Pa (5 bars).

Preferably, the disposable component is sterilisable. Suitable sterilisation methods include but are not limited to gamma irradiation, chemical treatment with antimicrobial agents such as ethylene oxide, and heating/autoclaving. By use of a sterilisable disposable component, there is no need to gamma irradiate the more sensitive and expensive reusable transducer. Re-calibration of the transducer is limited to a simple offset correction when changing the disposable component.

Preferably, the disposable component is composed of a material which is combustible. A range of suitable polymeric plastic materials are known which can be combusted. The advantage of using a combustible material is that it can be easily disposed of by incineration, thereby avoiding lengthy decontamination or cleansing procedures and has a low environmental load.

Preferably, the disposable component additionally comprises a sensor. Suitable sensors include, but are not limited to, temperature sensors, conductivity sensors and pH sensors. The advantages of combining the disposable component with an additional sensor is that it both optimises space usage on chromatography/purification system and it reduces the hold-up/dead volume of the system.

In a second aspect of the invention, there is provided a method for determining the pressure of a fluid using a multi-component part transducer assembly, wherein the assembly comprises a reusable component comprising a load cell;

a disposable component comprising a body having a container or conduit therein which defines a flow path for the fluid and a flexible membrane in pressure contact with the fluid; and a locking component to secure the reusable component to the disposable component in order to effect pressure contact between the load cell and the flexible membrane;

the method comprising the steps of:
a) securing the reusable component to the disposable component to effect pressure contact between the load cell of the reusable component and the flexible membrane of the disposable component;
b) filling the container or conduit with a fluid; and
c) determining the pressure of the fluid with the load cell.

Preferably, the reusable component additionally comprises an adapter attachable to the load cell, the adapter having one face for contact with the flexible membrane to effect pressure contact between the flexible membrane and the load cell, wherein step a) of the method involves securing the reusable component to the disposable component such that pressure contact between the load cell and the flexible membrane is effected by the adapter.

Contact between the load cell (or the adapter) and the flexible membrane is further enhanced by the inflexible or rigid nature of the load cell/adapter face which is in pressure contact with the flexible membrane as opposed to transducers known in the prior art which utilise pressure contact between two flexible membranes. The use of an inflexible or rigid face increases sensitivity by reducing the risk that any regions of the face are less responsive to pressure due to variations in flexibility.

Preferably, the step of securing the reusable component to the disposable component involves linearly aligning the components to maximise pressure contact between the load cell and the flexible membrane. Axial alignment also avoids any rotation of the parts which can lead to wear of the flexible membrane. More preferably, the assembly further comprises guide elements and the method involves linearly aligning the components by means of the guide elements.

Preferably, the disposable component is securable to the reusable component by the locking component such that a force of at least 10 N, and more preferably a force of at least 50 N, is required to separate the reusable component from the disposable component.

Preferably, the locking element is a yoke and the yoke secures the disposable component to the reusable component.

In a third aspect of the present invention, there is provided the method as hereinbefore described for use in the development or manufacture of a pharmaceutical or biotechnology product.

In a fourth aspect of the present invention, there is provided a system for separating and/or purifying chemical and/or biological compounds comprising the multi-component part transducer assembly as hereinbefore described and separation and/or filtration means.

Preferably, the separation means is a chromatography column, membrane, bed, expanded bed or fluidised bed.

Preferably, the filtration means is a cross-flow filter or a dead end filter.

Preferably, the system is for use in a pharmaceutical or biotechnology development or manufacturing facility.

In a fifth aspect of the present invention, there is provided a flow path kit for use in a chromatography or filtration system, comprising the disposable component of the multi-component part transducer assembly as hereinbefore described, connecting tubing, and one or more sensors. Preferably, the one or more sensors are disposable sensors.

Examples of such disposable sensors include, but are not limited to, UV detectors, pH sensors, temperature sensors, flow meters, ion-specific electrodes, conductivity sensors and biosensors. In a preferred embodiment, the disposable component additionally comprises the sensor. Preferably, the flow path kit is sterilisable. Most preferably, the flow path kit is combustible.

BRIEF DESCRIPTION OF THE DRAWINGS

FIGS. 1a-d show an embodiment of a multi-component transducer assembly according to the invention; FIG. 1a is a perspective view of the assembly showing the reusable and disposable components separated from each other; FIG. 1b is a perspective view of the assembly with the reusable and disposable components contacting each other; FIG. 1c is a perspective view in which the reusable and disposable components are secured together; and FIG. 1d is a plan view of the assembly of FIG. 1c.

FIGS. 2a-f show an embodiment of a reusable component and a disposable component in accordance with the invention; FIGS. 2a and 2b are exploded and perspective views of a disposable component, respectively; FIGS. 2c and 2d show exploded and perspective views of a reusable component comprising a load cell with an adapter; and FIGS. 2e and 2f are perspective views showing the load cell aligned for contact with the disposable component.

DETAILED DESCRIPTION OF THE INVENTION

Figure 3:
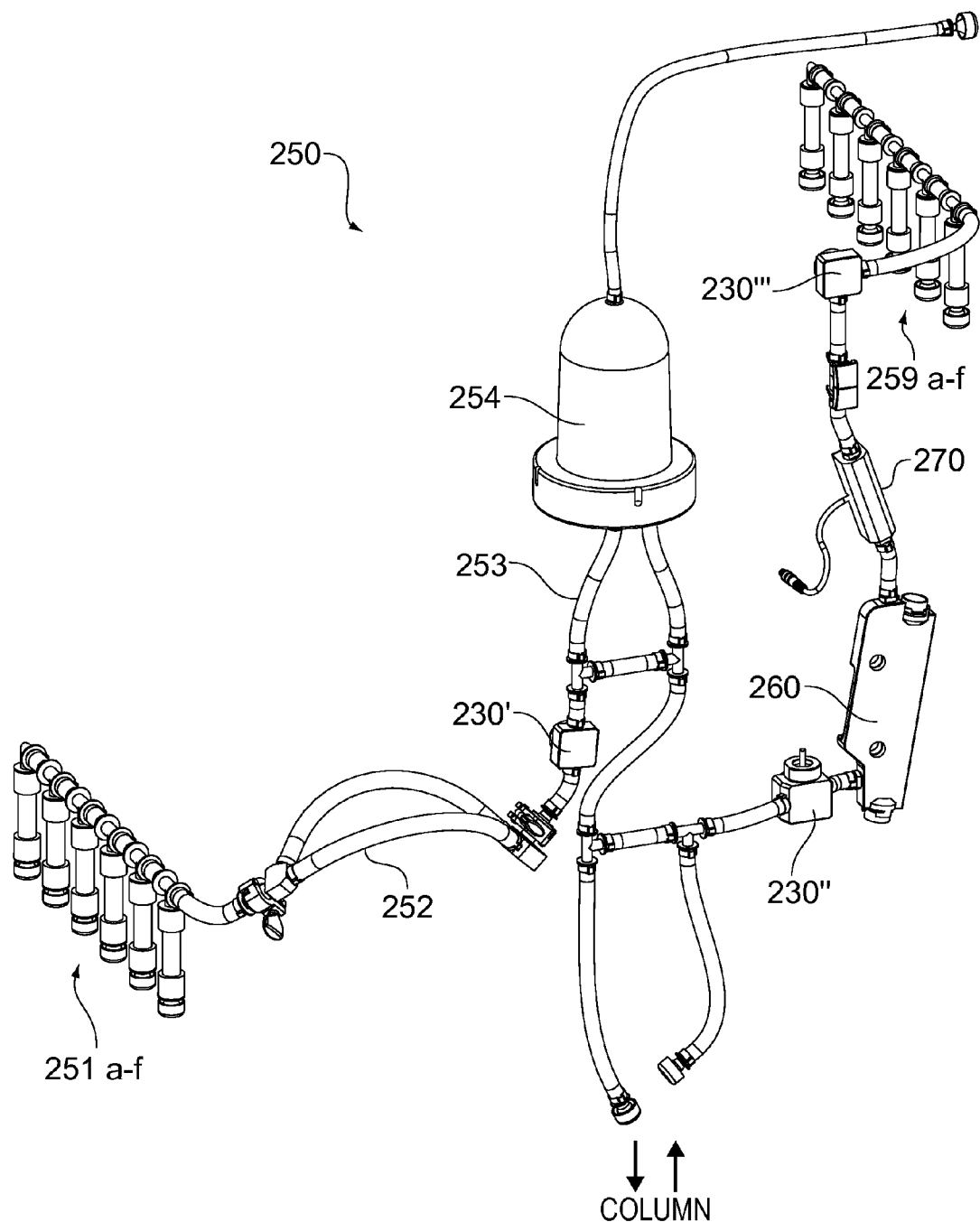
FIG. 3 shows a flow path kit for a chromatography system comprising disposable elements, including a disposable component of the multi-component part transducer assembly in accordance with the invention.

Embodiments of a multi-component part transducer assembly for measuring pressure in a fluid of interest are shown in the accompanying Figures.

FIG. 1a gives an exploded, perspective view of a multi-component part transducer assembly 10 comprising a reusable component 20, a disposable component 30 and a locking component 40.

The reusable component 20 comprises a housing or body 22 for a transducer 24 in the form of a load cell; the load cell may be any standard or conventional load cell (e.g. Futek model no. LCM300-50lb (223N), Sensotest Electronics AB, Sweden). In the embodiment shown in FIG. 1a the load cell 24 has an adapter or plunger 26 which is reversibly attachable to it and which can be interchanged with other adapters or plungers 26 of varying dimensions. One face 27 of the adapter 26 may be modified to maximise contact with the face of a flexible membrane or diaphragm (FIG. 2b) in the disposable component 30 which is required in use for determining pressure, when the reusable component 20 is brought into contact with the disposable component 30. This ability to select the adapter to correspond to the area of the flexible membrane used in the flow path allows the operator the flexibility of determining a wide range of pressures within the dynamic range of the load cell by simply changing the adapter. This has the advantage in that it both avoids the need to change transducers when moving from a low to high pressure application, and can result in greater accuracy depending upon the dynamic range of the load cell. The housing 22 is typically made of stainless steel. In the embodiment shown, the housing 22 is designed to affix to the body of an analytical or purification system, such as the ÄKTA™ system (GE Healthcare Bio-Sciences AB, Sweden) for biomolecule separation.

The disposable component 30 comprises a body 32 which has a conduit within it (not shown) which defines a flow path for the fluid of interest, the fluid entering the body 32 via inlet 34' and exiting via outlet 34". The body 32 is predominantly rectangular in shape with a sealing ring 31 protruding from its anterior face. The body 32 further comprises a flexible membrane or diaphragm (not shown), adjacent to face 33 of sealing ring 31, which is in pressure contact with the fluid of interest. The flexible membrane may be irreversibly affixed within the body or may be a replaceable/disposable element. The membrane is typically made of a suitable elastomeric or rubber material (e.g. ethylen propylene diene monomer rubber, EPDM, Industrigummi AB, Sweden) which will deform in a manner proportional to the pressure of the fluid with which it is in contact. In use, the inlet 34' and outlet 34" are connected to tubing (not shown), typically reinforced tubing which can withstand operating pressures required for pharmaceutical and biotechnological separations and purifications (e.g. at least $4 \times 10^5$ Pa, 4 bars and preferably $5 \times 10^5$ Pa, 5 bars). The tubing may have an internal diameter in excess 3 mm and preferably in excess of 6 mm, to facilitate the high flow rates required for such applications (e.g. 1 to 1000l/hr, preferably 10-500l/hr, most preferably 50l/hr) and may be attached to other sensors or separation/purification means such as temperature, conductivity, UV or pH detectors and chromatography columns or filters. The body 32 and its component parts (e.g. inlet 34'/outlet 34") can be made of any suitable material which can withstand the operating pressures associated with the separation/purification method. For pharmaceutical and biotechnological applications, it is preferable that that body parts are composed of materials which are suitable for GMP such as polymers which comply with the Code of Federal Regulations 177 (CFR 177) and United States Pharmacopeia VI (USP VI). Suitable polymers, which are also combustible, include polypropylene (e.g. Rochling Engineering Plastics, UK). The advantage of using a combustible material is that it can be easily disposed of by incineration. Preferably the body 32 and membrane (not shown) are composed of a material which can be sterilised by gamma irradiation and/or other means (e.g. chemical sterilisation or autoclaving) as it is important to minimise microbial contamination when working with biological fluids and/or pharmaceutical/biotechnological products. The body 32 may also comprise locating or receiving elements (not shown) which receive guide elements 42', 42" present on the locking component 40 to ensure that the reusable and disposable components are axially aligned. Axial alignment is important to maximise contact between the face 27 of the load cell adapter 26 and the flexible membrane (FIG. 2, 137).

It will be understood that in other embodiments, the body 32 could comprise a container therein and simply have a single inlet/outlet which defines a flow path. Other embodiments, in which the inlet 34' and outlet 34" are at right angles to each other rather than perpendicular to each other, are equally possible.

The two components 20, 30 are axially aligned and are then brought into contact with each other as shown in FIG. 1b.

In the embodiment shown, protruding guide elements 42', 42" (FIG. 1a) are used to effect contact along an essentially straight and axial line between the two components 20, 30 by co-locating with two receiving elements (FIG. 2b, 139' and 139"), in the form of female members, in the opposing rectangular face of the disposable component 20. Once the two components have been axially aligned and are brought into contact in this way, such that the opposing faces 23, 33 are in contact with each other, the components are locked into position by use of locking component 40.

The locking component 40 is provided to secure the reusable component 20 to the disposable component 30 once these two components are brought into contact with each other. The locking component 40 may be attached to the reusable component 20 as shown in the figure or it may be affixed to a separate element (for example, the body of an analytical or purification system) to which the reusable element can be connected.

In one embodiment (FIG. 1a), the locking component 40 takes the form of a yoke comprising a bar 44 which is free to pivot around legs 46', 46" and can be locked into position by means of adjustable screws 48', 48". The height of legs 46', 46" above face 23 of the reusable component is such that when the opposing faces 23, 33 are in contact with each other (as described above), bar 44 can be forced down onto the backing plate 35 by tightening screws 48', 48". In this way, an axial force of at least 10 N and preferably at least 50 N can be applied to press the two components 20, 30 together and lock them into position (FIG. 1c). The locking component can be manufactured from any suitable material, such as stainless steel or a polymeric plastic, which can withstand forces frequently encountered in biotechnological and pharmaceutical applications (i.e. typically in excess of 10 N and preferably in excess of 50 N). It will be understood that 'snap-fit' locking mechanisms are not suitable for use with the present invention because they are not strong enough for use in such applications.

When the reusable component 20 is secured to the disposable component 30 in the manner described above (FIG. 1c), there is pressure contact between the load cell 24 and the flexible membrane (FIG. 2b, 137) of the disposable component, mediated by the adapter 26. As the flexible membrane is in direct pressure contact with the fluid of interest in the flow path, the pressure of this fluid can be indirectly measured by the load cell as a force exerted on the adapter and thence on the load cell. This force can then be used to determine the pressure in the fluid, as the area of the adapter face in contact with the flexible membrane is known, from the relationship of Pressure=Force/Area. This pressure value can then be electronically transmitted to a visual display unit or stored in a database associated with the chromatography or filtration system to which the assembly is attached. The pressure value can also be used to signal an alarm if the value exceeds a predetermined threshold.

FIG. 1d shows an aerial plan view of the assembly shown in FIG. 1c; the disposable component 30 being secured to the reusable component 20 by means of the locking component 40.

The multi-component part transducer assembly of the invention can be used for a variety of applications to determine the pressure of a range of fluids; it will be understood that the term fluid includes both gases and liquids. The transducer assembly can be used in many applications, including those associated with water/waste analysis and purification, food and beverage manufacture and chemical processing. However, the transducer assembly of the invention finds particular utility in the development and manufacture of pharmaceutical and biotechnological products where it can be used in combination with separation, purification and chemical synthesis systems for determining the pressure of liquids which contain chemical and biological compounds of interest. Typical examples of such liquids include bioprocess solutions and/or suspensions, blood, plasma, fermentation and cell culture products. Examples of chemical and biological compounds of interest, which might be present in such liquids, include proteins, peptides, antibodies, vaccines, glycoproteins, lectins, drugs, carbohydrates, lipids, and chemical intermediates.

FIG. 2a shows an exploded view of the disposable component 30 of FIG. 1. In the figure, the component 130 is seen to comprise a body 132 which is predominantly rectangular in shape having an inlet 134' and outlet 134" and an open threaded ring 136 protruding from its anterior face. The body 132 is hollowed, having a conduit within it which is in fluid communication with the inlet 134' and outlet 134" which thus defines a flow path for the entry and exit of liquid. A flexible membrane or diaphragm 137 can be positioned across the face of the ring 136 and secured in position by means of a retaining ring 138 and threaded locking spacing ring 131 to form a fluid tight seal, as seen in FIG. 2b. In this position, the flexible membrane 137 is in pressure contact with the fluid or liquid within the conduit and flow path. As described above, the body parts which come into contact with the fluid can be made of any suitable materials but preferably those which comply with GMP, CFR 177 and USP VI, are free of animal origin and are sterilisable for pharmaceutical and/or biotechnological applications. Typically the body 132 and locking ring 131 are made of a rigid plastic material such as polypropylene. Membrane 137 can be formed from appropriate materials which provide a seal with the fluid of interest and are strong enough and flexible enough to respond to and transmit the pressures exerted by the fluid. EPDM membranes, produced by GE Design and supplied by Industrigummi AB, Sweden are particularly suitable. The diameter, and hence the area, of the membrane to be used is selected on the basis of the pressure to be determined, diameters typically ranging from 1 to 10 cm (i.e. corresponding to an area of range 0.7 $cm^2$ to 78.5 $cm^2$); a diameter of 2 cm (i.e. area of 3.14 $cm^2$) is preferred to determine pressures of at least $5\times10^5$ Pa (5 bar).

In the front, perspective view of FIG. 2b the disposable component 130 has been assembled and shows membrane 137 in its final position in fluid communication with a fluid within the flow path. Receiving elements 139', 139" are shown which receive protruding guide elements (FIG. 1a, 42', 42") on the locking component (FIG. 1, 40) to facilitate the axial alignment and contact of the opposing faces (133 and 23) of the disposable (30, 130) and reusable components (20).

FIGS. 2c and 2d illustrate the replaceable or changeable nature of the adapter 126 on the load cell 124. The adapter 126 or plunger can be changed, depending upon the pressure of the fluid to be determined, to provide a modified surface or face 127 for contact with the flexible membrane. Thus, for example, different adapters 126 can be used which have faces 127 of differing areas for contact with the flexible membrane 137. In this way, the load cell 124 and adapter 126 provide a greater flexibility, in terms of the range of pressures which can be determined, and increased accuracy of determination compared to conventional pressure sensors which are used for measuring pressures in a fluid. The face 127 of the adapter may also be somewhat convex in nature to aid removal of any air bubbles within the fluid which have become trapped against the interior surface of the flexible membrane 137; the air bubbles being displaced from the membrane when the adapter 126 is in pressure contact with the membrane 137.

The load cell 124 with adapter 126 affixed must be aligned at right angles to the flexible membrane 137 of disposable unit 130 in order to ensure maximum overlap between the adapter face 127 and membrane 137 when these components are in contact. FIGS. 2e and 2f schematically depict the positioning of the load cell 124 and disposable unit prior to bringing these two components together into pressure contact with each other. The two components are axially aligned and brought together such that there is pressure contact between the load cell 124 and the flexible membrane 137, mediated through the adapter 126, by means of the locking component 40 as described above in FIG. 1.

FIG. 3 shows a disposable flow path kit for a chromatography system, including disposable components of the multi-component part transducer assembly in accordance with the invention. Such flow path kits are relatively inexpensive and provide the user with pre-sterilised, ready-to-use components which can be easily installed in a chromatography system. The flow path kit 250 is suitable for use with, for example, an ÄKTA™ system (GE Healthcare Bio-Sciences AB, Sweden) for biomolecule separation.

The flow path kit 250 consists of disposable components which can all be replaced after a single or a few uses by the operator of the chromatography system. The flow path 250 is first connected to a suitable chromatography system which would include a reusable component and locking component as described above (not shown but see, for example, FIGS. 1, 20 and 40). The disposable components (230', 230", 230''') are then secured to their respective reusable components to effect pressure contact between the transducer and the flexible membrane, by means of the locking component (not shown) as previously described.

Liquid flow is controlled by pinch valves which are not shown in the figures. In use, liquids to be processed are aspirated via inlets 251*a-f*, transferred via tubing 252, 253 to air trap 254 to remove air bubbles, separated on a chromatography column (not shown) and then collected from outlets 259*a-f*. A number of sensors are used to monitor operating conditions during this process, including pressure (reusable components 230', 230" and 230'''), fluid speed (flow cell 260) and conductivity (conductivity meter 270); other parameters such as temperature, UV absorbance and pH can also be monitored by suitable disposable sensors. As can be seen from the diagram, pressure is monitored at three separate locations along the flow path by means of disposable components 230', 230" and 230'''. Disposable component 230" can be seen to additionally comprise a pH sensor.

It will be understood that flow path kits including disposable components of the multi-component transducer assembly of the invention can also be used for other applications such as filtration systems, solid phase synthesis systems on fixed beds, and systems based upon membrane adsorption or charge.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A multi-component part transducer assembly for determining the pressure in a fluid of interest, said assembly comprising
   a reusable component comprising a transducer;
   a disposable component comprising a body having a container or conduit therein which defines a flow path for said fluid and a flexible membrane in pressure contact with the fluid; and
   a locking component to secure said reusable component to said disposable component in order to effect pressure contact between said transducer and said flexible membrane;
   wherein said transducer is a load cell; and
   wherein said locking component is a yoke comprising a bar which is free to pivot around legs and can be locked into positions by means of adjustable screws, whereby an axial force of at least 10 N can be applied to press the reusable and disposable components together and lock them into position.

2. The assembly of claim 1, wherein said reusable component additionally comprises an adapter attachable to said load cell having one face for contact with the flexible membrane to effect pressure contact between the flexible membrane and the load cell.

3. The assembly of claim 2, wherein said one face of said adapter is modified to maximise contact between the face and the flexible membrane.

4. The assembly of claim 2, wherein said one face of the adapter is either planar or convex.

5. The assembly of claim 2, wherein the adapter is reversibly attachable to the load cell.

6. The assembly of claim 2, wherein the area of the one face of the adapter can be varied to correspond to the area of the flexible membrane.

7. The assembly of claim 1, wherein said flow path has an internal diameter in excess of 6 mm.

8. The assembly of claim 1, wherein in use an inlet and an outlet of the disposable component are connected to reinforced tubing.

9. The assembly of claim 8, wherein said reinforced tubing is capable of withstanding a pressure of at least $4 \times 10^5$ Pa (4 bars).

10. The assembly of claim 8, wherein the reinforced tubing is capable of withstanding a pressure of at least $5 \times 10^5$ Pa (5 bars).

11. The assembly of claim 1, wherein said disposable component is sterilisable.

12. The assembly of claim 1, wherein the disposable component additionally comprises a sensor.

13. The assembly of claim 12, wherein said sensor is selected from the group consisting of temperature sensor, conductivity sensor and pH sensor.

14. A system for separating or filtering target compounds comprising the multi-component part transducer assembly of claim 1 and separation means.

15. The system of claim 14, wherein said separation means is a chromatography column, membrane, bed, expanded bed or fluidised bed.

16. The system of claim 14, wherein said filtration means is a cross-flow filter or a dead end filter.

17. A flow path kit for use in a chromatography or filtration system, comprising the multi-component part transducer assembly of claim 1, connecting tubing, and one or more sensors.

18. The flow path kit of claim 17, wherein said one or more sensors are disposable.

19. A method for determining the pressure of a fluid using a multi-component part transducer assembly, wherein said assembly comprises
   a reusable component comprising a load cell;
   a disposable component comprising a body having a container or conduit therein which defines a flow path for said fluid and a flexible membrane in pressure contact with the fluid; and
   a locking component to secure said reusable component to said disposable component in order to effect pressure contact between said load cell and said flexible membrane;
said method comprising the steps of:

a) securing said reusable component to said disposable component to effect pressure contact between said load cell of the reusable component and said flexible membrane of the disposable component;
b) filling the container or conduit with a fluid; and
c) determining the pressure of said fluid with said load cell wherein said locking component is a yoke comprising a bar which is free to pivot around legs and can be locked into positions by means of adjustable screws, whereby an axial force of at least 10 N can be applied to press the reusable and disposable components together and lock them into position.

20. The method of claim 19, wherein the reusable component additionally comprises an adapter attachable to the load cell, said adapter having one face for contact with the flexible membrane to effect pressure contact between the flexible membrane and the load cell, wherein step a) of the method involves securing the reusable component to the disposable component such that pressure contact between the load cell and the flexible membrane is effected by the adapter.

21. The method of claim 19, wherein the step of securing the reusable component to the disposable component involves linearly aligning said components to maximise pressure contact between the load cell and the flexible membrane.

22. The method of claim 21, wherein the assembly further comprises guide elements and the method involves linearly aligning the components by means of said guide elements.

\* \* \* \* \*